(12) United States Patent
Yamaguchi et al.

(10) Patent No.: US 8,579,799 B2
(45) Date of Patent: Nov. 12, 2013

(54) ELECTRONIC ENDOSCOPE SYSTEM, PROCESSOR FOR ELECTRONIC ENDOSCOPE, IMAGE SEARCH SYSTEM, AND IMAGE SEARCH METHOD

(75) Inventors: Hiroshi Yamaguchi, Kanagawa (JP); Takayuki Iida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 176 days.

(21) Appl. No.: 13/163,542

(22) Filed: Jun. 17, 2011

(65) Prior Publication Data

US 2011/0319711 A1 Dec. 29, 2011

(30) Foreign Application Priority Data

Jun. 29, 2010 (JP) ................................ 2010-147286

(51) Int. Cl.
*A61B 1/04* (2006.01)
(52) U.S. Cl.
USPC ........... 600/109; 600/118; 600/160; 600/178; 600/323; 600/476
(58) Field of Classification Search
CPC .................................................. A61B 1/00009
USPC ................. 600/109, 118, 160, 178, 323, 328, 600/476–478; 348/68, 74; 705/2
See application file for complete search history.

(56) References Cited

U.S. PATENT DOCUMENTS

| | | | | |
|---|---|---|---|---|
| 4,737,912 A * | 4/1988 | Ichikawa | ........................ | 600/301 |
| 4,914,512 A * | 4/1990 | Sekiguchi | ........................ | 348/71 |
| 5,029,016 A * | 7/1991 | Hiyama et al. | ................ | 358/403 |
| 5,111,306 A * | 5/1992 | Kanno et al. | ................... | 358/403 |
| 5,615,112 A * | 3/1997 | Sheng et al. | ........................ | 1/1 |
| 5,640,553 A * | 6/1997 | Schultz | ................................... | 1/1 |
| 7,920,732 B2 * | 4/2011 | Shimizu et al. | ................ | 382/128 |
| 8,328,712 B2 * | 12/2012 | Nishiyama et al. | ........... | 600/109 |
| 2003/0176768 A1 * | 9/2003 | Gono et al. | ..................... | 600/109 |
| 2005/0075537 A1 * | 4/2005 | Chen et al. | ..................... | 600/109 |

(Continued)

FOREIGN PATENT DOCUMENTS

| | | |
|---|---|---|
| JP | 4-17076 (A) | 1/1992 |
| JP | 2002-95625 A | 4/2002 |
| JP | 2006-166940 (A) | 6/2006 |
| WO | WO 2009/061008 A1 | 5/2009 |

OTHER PUBLICATIONS

Notification of Reason(s) for Refusal dated Sep. 25, 2013, with English translations.

*Primary Examiner* — John P Leubecker
(74) *Attorney, Agent, or Firm* — McGinn IP Law Group, PLLC

(57) ABSTRACT

In a search mode of an electronic endoscope system, ordinary light images and special light images are captured from a body cavity respectively under white light and special light. Simultaneously, biological information on the body cavity is acquired from image signals obtained under the special light. The ordinary and special light images are associated with the acquired biological information and stored in an image accumulator. By pressing a lock-on switch while confining a target in an area designating frame on an ordinary image on a monitor, the target is designated and biological information on the target is determined. Thereafter, biological information associated with the latest image in the image accumulator is compared with the biological information on the search target. If the latest image contains an area having the same biological information as the search target, the area designating frame is displayed on that area on the monitor.

13 Claims, 15 Drawing Sheets

(56) References Cited

U.S. PATENT DOCUMENTS

| | | | |
|---|---|---|---|
| 2005/0124858 A1* | 6/2005 | Matsuzawa et al. | 600/176 |
| 2009/0227837 A1* | 9/2009 | Shimizu et al. | 600/109 |
| 2009/0262225 A1* | 10/2009 | Yamaguchi et al. | 348/265 |
| 2010/0030021 A1* | 2/2010 | Minai et al. | 600/109 |
| 2010/0150416 A1* | 6/2010 | Kim et al. | 382/128 |
| 2010/0158330 A1* | 6/2010 | Guissin et al. | 382/128 |
| 2010/0265354 A1* | 10/2010 | Kameyama | 348/222.1 |
| 2011/0077462 A1* | 3/2011 | Saitou et al. | 600/109 |
| 2011/0237884 A1* | 9/2011 | Saito | 600/109 |
| 2011/0237915 A1* | 9/2011 | Yamaguchi | 600/339 |
| 2011/0301443 A1* | 12/2011 | Yamaguchi et al. | 600/324 |
| 2012/0002026 A1* | 1/2012 | Honda et al. | 348/65 |
| 2012/0139936 A1* | 6/2012 | Horn et al. | 345/589 |
| 2012/0183134 A1* | 7/2012 | Malone | 380/28 |

* cited by examiner

FIG.5A
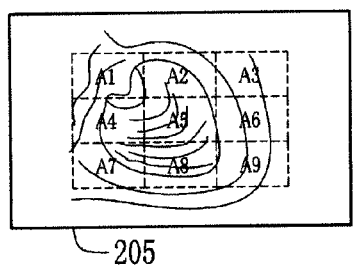
FIG.5B
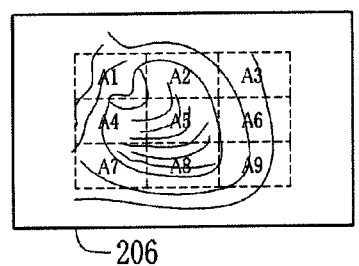
FIG.5C
| A1 D:M2 C:M1 StO2:H1 | A2 D:S1 C:L1 StO2:M2 | A3 D:S1 C:L2 StO2:L1 |
| --- | --- | --- |
| A4 D:S2 C:H1 StO2:M2 | A5 D:D2 C:H2 StO2:L2 | A6 D:M1 C:M1 StO2:L3 |
| A7 D:M1 C:M2 StO2:M2 | A8 D:M2 C:H1 StO2:M1 | A9 D:S1 C:L2 StO2:H2 |
FIG.6
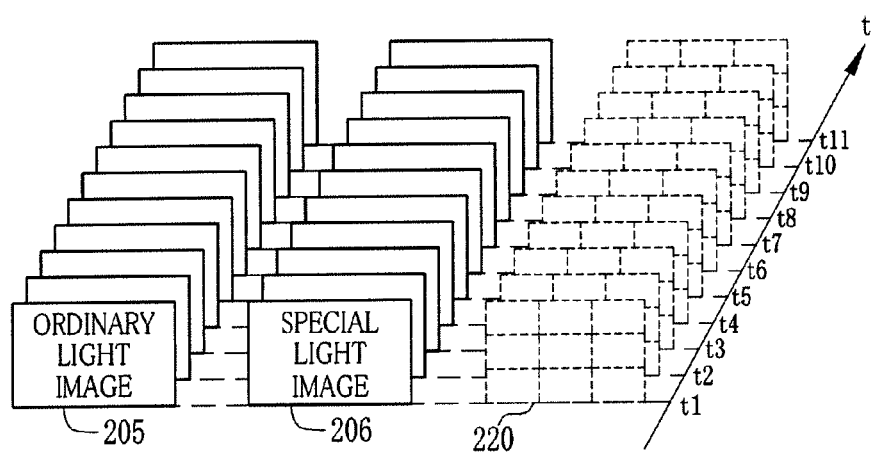

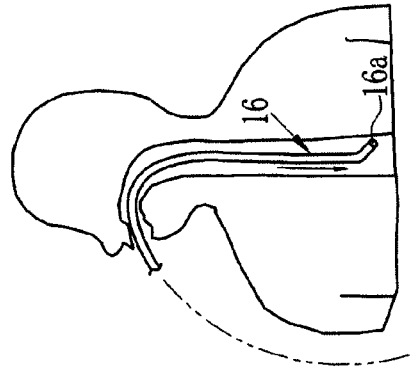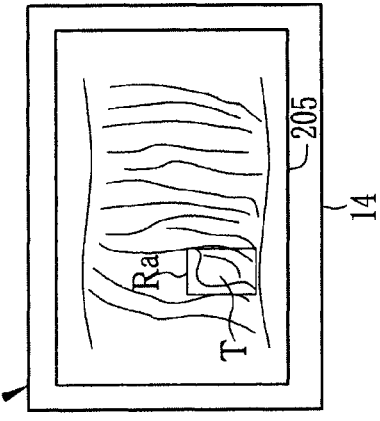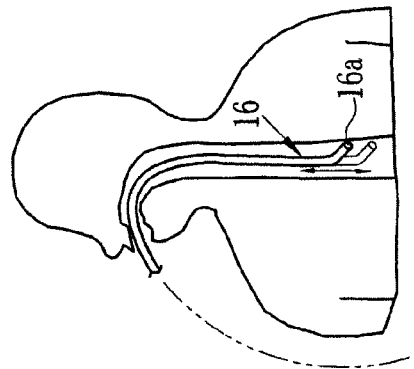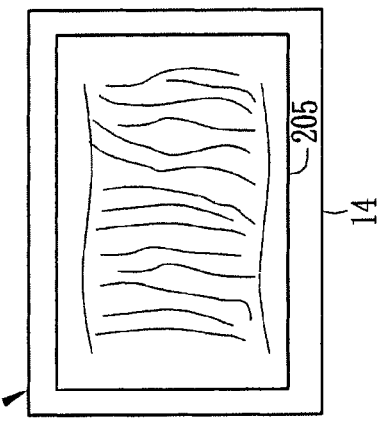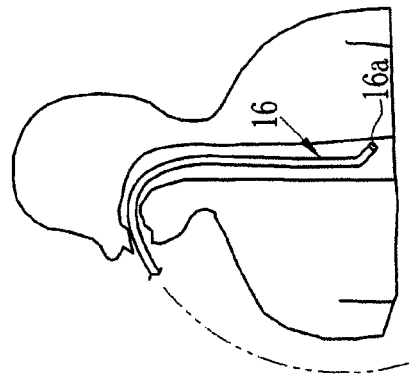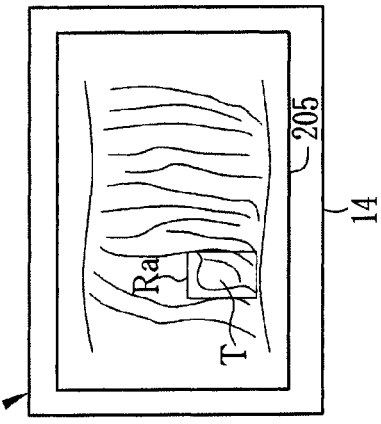

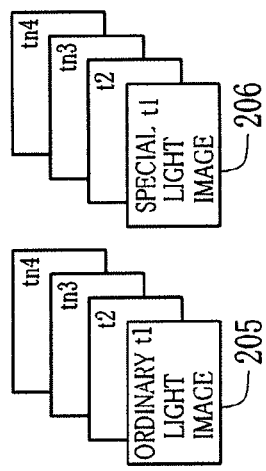
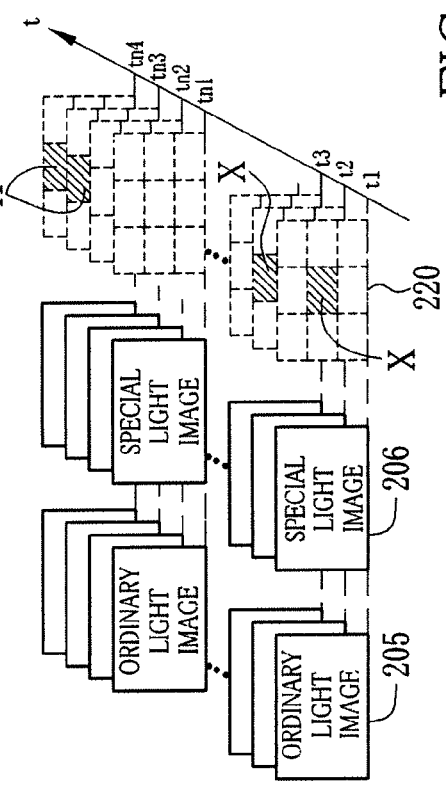
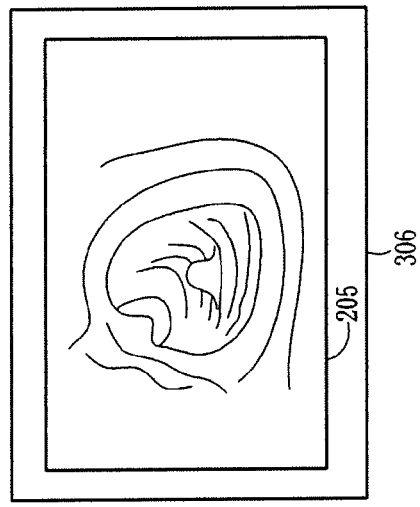

ELECTRONIC ENDOSCOPE SYSTEM, PROCESSOR FOR ELECTRONIC ENDOSCOPE, IMAGE SEARCH SYSTEM, AND IMAGE SEARCH METHOD

FIELD OF THE INVENTION

The present invention relates to an electronic endoscope system that can search for a target such as a pathologic lesion among a group of images captured through an electronic endoscope. The present invention also relates to a processor for the electronic endoscope, an image search system and an image search method therefor.

BACKGROUND OF THE INVENTION

In recent medical field, electronic endoscopes are frequently used for diagnoses and treatments. The electronic endoscope has a probing portion that is inserted into a body cavity of a subject under inspection, and an imaging unit including a CCD or the like is incorporated in a distal end of the probing portion. The electronic endoscope is also connected to a light source unit, so that light from the light source unit is projected from the distal end of the probing portion to illuminate the inside of the body cavity. While the inside of the body cavity is being illuminated, subject tissues inside the body cavity are imaged by the imaging unit. Captured images are processed in various ways in a processor which is also connected to the electronic endoscope, and the processed images are displayed on a monitor.

The electronic endoscope thus visualizes the inside of the body cavity of the subject under inspection in real time fashion. The captured images of the interior of the body cavity not only show the whole subject tissues but also individual details of the subject tissues, including fine or capillary vessels, deep blood vessels, pit patterns or gland orifice structures, as well as tissue surface asperities like concavity and convexity. Observing the condition of the subject tissues as the whole and in detail allows making diagnoses as to whether there are any lesions like a tumor.

When the operator of the endoscope detects a lesion from the image of the body cavity, the operator will usually scan the periphery around the detected lesion to search for metastasis of this lesion. For this purpose, the operator moves the distal end of the probing portion up and down or turns the direction of the distal end inside the cavity. However, the initially-detected lesion tends to fade out of the monitor screen with the up-down movement of the distal end of the probing portion. In order to trace a target like a lesion after the endoscope lose sight of the target, JPA 2002-095625 suggests detecting feature points of the target from endoscopic images and tracing the target with reference to its feature points.

However, once the detected feature points have faded out of the screen, it can be hard to detect the same feature points exactly through pattern recognition. Especially when the feature points represent a polyp in a deep labyrinth area of subject tissues, pattern recognition cannot ensure exact detection of the identical feature point.

SUMMARY OF THE INVENTION

The present invention has an object to provide an electronic endoscope system, a processor for an electronic endoscope, an image search system, and an image search method, which make it possible to trace a lesion like a polyp accurately and steadily even after a doctor or operator of the endoscope loses sight of the lesion during the endoscopic probing.

An electronic endoscope system of the present invention comprises an imaging device, an image producing device, a special light projecting device, a biological information acquiring device, an associating device, an input device, and a search device. The imaging device obtains image signals through imaging of an interior of a body cavity at constant intervals. The image producing device produces images sequentially based on the image signals. The special light projecting device projects special light into the body cavity, the special light having a different wavelength range from white light. The biological information acquiring device acquires biological information from image signals obtained while the special light is being projected into the body cavity. The associating device associates the biological information acquired by the biological information acquiring device with an image corresponding to the image signal from which this biological information has been acquired. The input device inputs biological information on a search target. The search device searches for an image that is associated with the same biological information as the input biological information on the search target among the images which have been associated with the biological information by the associating device.

Preferably, the electronic endoscope system further includes a display device for displaying images produced by the image producing device, an area designating frame display device for displaying an area designating frame on an image displayed on the display device, and a lock-on device for designating a portion confined in the area designating frame as a search target, wherein the input device inputs the biological information on the designated search target on the basis of biological information acquired from the image signal obtained at the time when the search target is designated. When an image associated with the same biological information as the input biological information on the search target is displayed on the display device, the area designating frame display device preferably displays the area designating frame on a portion of the displayed image, the portion corresponding to the biological information on the search target.

Preferably, the electronic endoscope system further includes a white light projecting device for projecting white light into the body cavity. In this embodiment, the image producing device produces special light images from image signals obtained through imaging the interior of the body cavity illuminated with the special light, and ordinary light images from image signals obtained through imaging the interior of the body cavity illuminated with the white light. The associating device associates the biological information acquired by the biological information acquiring device with a special light image or an ordinary light image that corresponds to the image signal from which this biological information has been acquired, and the search device searches for those special or ordinary light images which are associated with the same biological information as the biological information on the designated search target.

The biological information acquired by the biological information acquiring device preferably includes vascular information including at least one of blood vessel depth, blood concentration, and oxygen saturation.

In a preferred embodiment, the special light projecting device is adapted to project at least three narrowband rays onto subject tissues including blood vessels in the body cavity. These at least three narrowband rays preferably have different wavelength ranges from each other within a range of 400 nm to 600 nm, including a blue ray band and a green ray band. The biological information acquiring device preferably includes a first narrowband signal obtaining device for obtaining a plurality of narrowband signals corresponding respectively to the narrowband rays from among the image signals obtained by the imaging device, and a first vascular information acquiring device for acquiring vascular information including information on blood vessel depth and blood concentration on the basis of the plurality of narrowband signals.

Preferably, the first narrowband signal obtaining device obtains first and second narrowband signals corresponding to first and second narrowband rays having different wavelength ranges from each other in the blue ray band, and a third narrowband signal corresponding to a third narrowband ray in the green ray band. Preferably, the first narrowband ray has a wavelength range of 405±10 nm, the second narrowband ray has a wavelength range of 470±10 nm, and the third narrowband ray has a wavelength range of 560±10 nm.

In a preferred embodiment, the special light projecting device is adapted to project a plurality of narrowband rays onto subject tissues including blood vessels in the body cavity. The plurality of narrowband rays preferably have different wavelength ranges from each other, at least one of the different wavelength ranges having a center wavelength of 450 nm or less. The biological information acquiring device preferably includes a second narrowband signal obtaining device for obtaining a plurality of narrowband signals corresponding respectively to the narrowband rays from among the image signals, and a second vascular information acquiring device for acquiring vascular information including information on blood vessel depth and oxygen saturation on the basis of the plurality of narrowband signals. Preferably, each of the plurality of narrowband rays includes a wavelength, to which oxygenated hemoglobin shows a different degree of light absorbance from reduced hemoglobin, and the plurality of narrowband signals vary differently from each other depending on oxygen saturation of blood.

In another aspect of the present invention, an image search system comprises an image accumulator, an input device, and a search device. The image accumulator stores special light images obtained through imaging an interior of a body cavity illuminated with special light that has a different wavelength range from white light, in association with biological information on the body cavity acquired at the same time as the special light images. The input device inputs biological information on a search target. The search device searches for those special light images which are associated with the same biological information as the input biological information on the search target among the special light images stored in the image accumulator.

In still another aspect of the present invention, a processor for an electronic endoscope comprises a receiving device for receiving image signals that are obtained at constant intervals by the electronic endoscope through imaging an interior of a body cavity illuminated with special light having a different wavelength range from white light. The processor also comprises an image producing device for producing special light images sequentially from the image signals, a biological information acquiring device for acquiring biological information on the interior of the body cavity from the image signals, an input device for inputting biological information on a search target, and a search device for searching for those special light images which are associated with the same biological information as the input biological information on the search target.

An image search method of the present invention comprises the following steps:

producing special light images sequentially based on image signals obtained through imaging an interior of a body cavity at constant intervals while projecting special light into the interior of the body cavity, the special light having a different wavelength range from white light; acquiring biological information on the interior of the body cavity from the image signals; associating the acquired biological information with the special light images; inputting biological information on a search target; and searching for those special light images which are associated with the same biological information as the input biological information on the search target.

According to the present invention, the endoscope can keep trace of a target such as a polyp in a body cavity accurately and steadily through searching those special light images which are associated with biological information on the target, even after the endoscope loses sight of the target as a result of push-pull movement of the endoscope inside the body cavity during the imaging.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5A is an explanatory diagram illustrating an ordinary light image captured under the illumination of ordinary light, virtually subdivided into nine segments;

FIG. 5B is an explanatory diagram illustrating a special light image captured under the illumination of special light, virtually subdivided into nine segments correspondingly to the ordinary light image of FIG. 5A;

FIG. 5C is an explanatory diagram illustrating vascular information on the respective segments of the ordinary or special light image;

FIG. 6 is an explanatory diagram illustrating ordinary light images, special light images, and vascular information on these images stored time-sequentially in an image accumulator;

FIG. 8A is an explanatory diagram illustrating a position of the endoscope distal end in the body cavity and an image of the body cavity inner wall surface captured in this position;

FIG. 8B is an explanatory diagram illustrating a position of the endoscope distal end in the body cavity proximal to the position of FIG. 8A and an image of the body cavity inner wall surface captured in this position;

FIG. 8C is an explanatory diagram illustrating a position of the endoscope distal end inserted deeper in the body cavity than the position of FIG. 8B and an image of the body cavity inner wall surface captured in this position;

FIGS. 19A-19C are explanatory diagrams illustrating a sequence of image-searching in the image search system.

DESCRIPTION OF THE PREFERRED EMBODIMENTS

Figure 1:
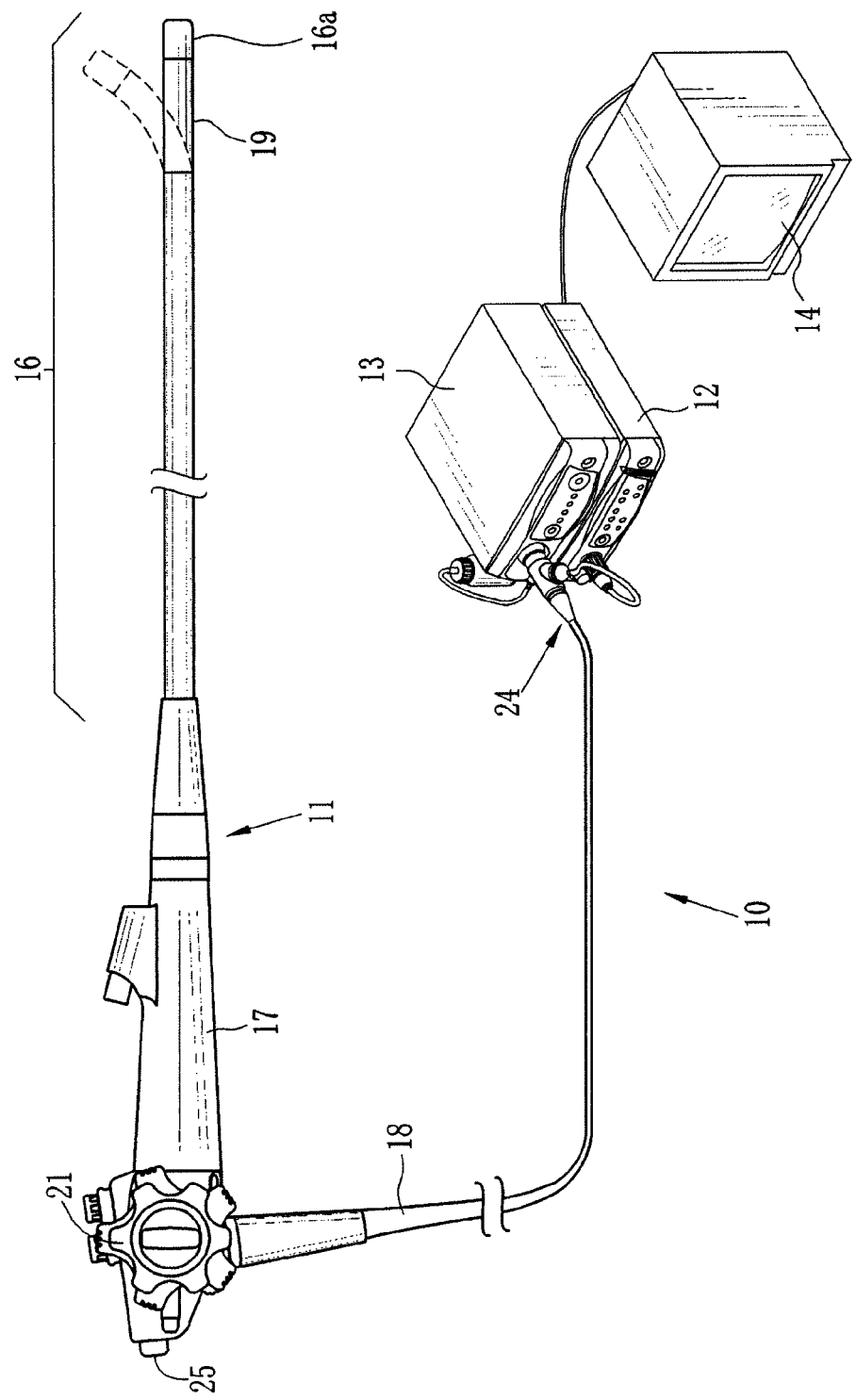
FIG. 1 is a diagram illustrating an outer appearance of an electronic endoscope system according to a first embodiment of the present invention.

As shown in FIG. 1, an electronic endoscope system 10 according to the first embodiment of the present invention includes an electronic endoscope 11, a processor 12, a light source unit 13 and a monitor 14. The endoscope 11 images the interior of a body cavity of a subject under inspection. The processor 12 produces images of the tissues inside the body cavity from electronic signals from the endoscope 11. The light source unit 13 provides light for illuminating the inside of the body cavity. The monitor 14 displays the images of the interior of the body cavity. The electronic endoscope 11 includes a flexible probing portion 16 to be inserted into the body cavity, a handling portion 17 coupled to a proximal end of the probing portion 16, and an universal cord 18 connecting the handling portion 17 to the processor 12 and the light source unit 13.

The probing portion 16 has a curving distal end that consists of serially linked segments. The curving portion 19 may curve in any directions in response to the operation on an angle knob 21 of the handling portion 17. A tip portion 16a formed in the distal end of the curving portion 19 contains an optical system for imaging the interior of the body cavity. The tip portion 16a may be oriented to any desirable direction inside the body cavity through the curving portion 19.

The cord 18 has a connector 24 to be coupled to the processor 12 and the light source unit 13. The connector 24 is a complex connector consisting of a connector terminal for data communication and a connector terminal for light source. Through this connector 24, the electronic endoscope 11 may be removably connected to the processor 12 and the light source unit 13.

Figure 2:
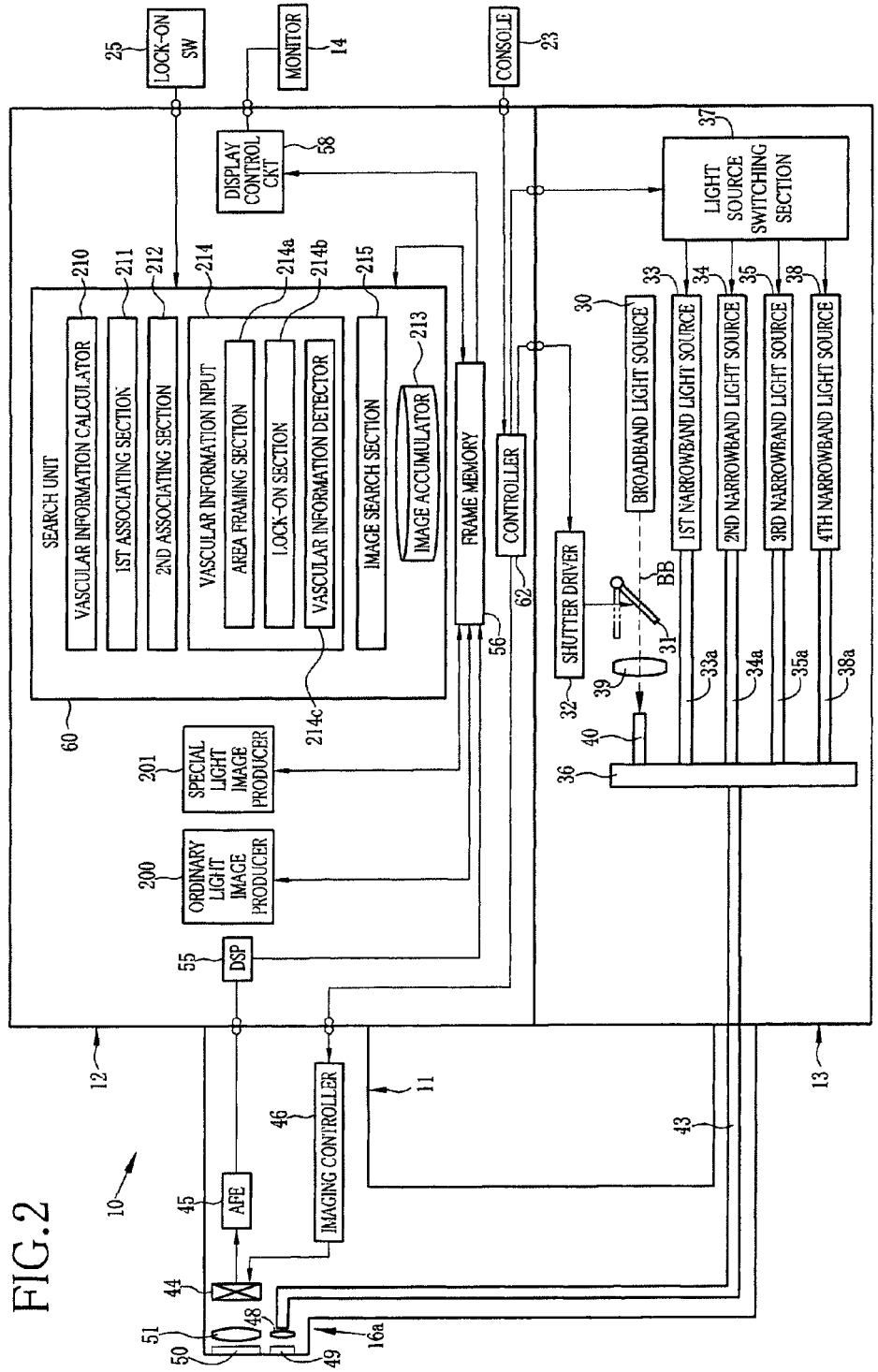
FIG. 2 is a block diagram illustrating the circuitry of the electronic endoscope system of the first embodiment.

As shown in FIG. 2, the light source unit 13 includes a broadband light source 30, a shutter 31, a shutter driver 32, first to fourth narrowband light sources 33 to 35 and 38, a photo-coupler 36, and a light source switching section 37. The broadband light source 30 may be a xenon lamp, white LED or micro-white light source, which emits broadband light BB having wavelengths ranging from the red ray region to the blue ray region (about 470 nm to 700 nm). The broadband light source 30 is kept ON while the electronic endoscope 11 is in operation. The broadband light BB from the broadband light source 30 is converged through a condenser lens 39 and then introduced into a broadband optical fiber 40.

A shutter 31 is installed in between the broadband light source 30 and the condenser lens 39, to be movable into a light path of the broadband light BB to block the broadband light BB, or out of the light path to allow the broadband light BB to travel to the condenser lens 39. A shutter driver 32 is connected to a controller 62, to control driving the shutter 31 according to instructions from the controller 62. The controller 62 is included in the processor 12.

The first to fourth narrowband light sources 33 to 35 and 38 may be laser diodes or the like. The first to fourth narrowband light sources 33 to 35 and 38 emit first to fourth narrowband rays N1, N2, N3 and N4, respectively. The first narrowband ray N1 is a blue ray of a wavelength limited to 400±10 nm, preferably to 405 nm, the second narrowband ray N2 is a blue ray of a wavelength limited to 470±10 nm, preferably to 473 nm, the third narrowband ray N3 is a green ray of a wavelength limited to 560±10 nm, preferably to 560 nm, and the fourth narrowband rays N4 is a ray of a wavelength limited to 440±10 nm, preferably to 445 nm. The first to fourth narrowband light sources 33 to 35 and 38 are coupled to the first to fourth narrowband optical fibers 33a to 35a and 38a respectively, so that the first to fourth narrowband rays N1 to N4 from the respective light sources are introduced into the first to fourth narrowband optical fibers 33a to 35a and 38a respectively.

The coupler 36 couples the broadband optical fiber 40 and the first to fourth narrowband optical fibers 33a to 35a and 38a to a light guide 43 in the electronic endoscope. Thus, the broadband light BB can enter the light guide 43 via the broadband optical fiber 40. On the other hand, the first to fourth narrowband rays N1 to N4 can enter the light guide 43 through the first to fourth narrowband optical fibers 33a to 35a and 38a respectively.

The light source switching section 37 is connected to the controller 62 in the processor 12, to turn the first to fourth narrowband light sources 33 to 35 and 38 ON or OFF according to the instruction from the controller 62. In an ordinary inspection mode, the broadband light source 30 is turned ON to illuminate the inside of body cavity with the broadband light BB to capture a broadband light image, whereas the first to fourth narrowband light sources 33 to 35 and 38 are turned OFF. On the other hand, in a search mode for extracting a search target, such as a lesion, from captured images, two kinds of processes will be executed under different illuminating conditions: ordinary light image capturing process, and special light image capturing process.

In the ordinary light image capturing process, the broadband light BE is projected into the body cavity to capture broadband light images, while the first to fourth narrowband light sources 33 to 35 and 38 are OFF, like in the ordinary inspection mode. In the special light image capturing process, the shutter 31 is inserted into the light path of the broadband light BB to block it from the body cavity. When the broadband light BB is blocked, the first narrowband light source 33 is first turned on through the light source switching section 37.

Then, while the first narrowband ray N1 is illuminating the body cavity, imaging of the subject tissues is carried out. When the imaging is complete, the controller 62 outputs an instruction to switch over the light source, upon which the first narrowband light source 33 is turned OFF, and the second narrowband light source 34 is turned ON. Thereafter when an image has been captured from the body cavity under the illumination of the second narrowband, the second narrowband light source 34 is turned OFF, and the third narrowband light source 35 is turned ON. When another image has been captured under the illumination of the third narrowband ray N3, the third narrowband light source 35 is turned OFF, and the fourth narrowband light source 38 is turned ON. Then another image is captured under the fourth narrowband ray N4 and, thereafter, the fourth narrowband light source 38 is turned OFF.

The electronic endoscope 11 includes the light guide 43, a CCD 44, an analog front end (AFE) 45, and an imaging controller 46. The light guide 43 may be a large-diameter optical fiber or a handle fiber, which has an inlet end inserted into the coupler 36 in the light source unit 13. An outlet end of the light guide 43 is opposed to a projection lens 48 that is mounted in the tip portion 16a. The light from the light source unit 13 is conducted through the light guide 43 and then outputs to the projection lens 48. The light entering the projection lens 48 is projected into the body cavity through a lightening window 49 that is mounted in a face end of the tip portion 16a. The broadband light BB and the first to fourth narrowband rays N1 to N4 are individually reflected from the body cavity, and then fall on a condenser lens 51 through an observation window 50 that is mounted in the face end of the tip portion 16a.

The CCD 44 may be a monochrome CCD. The CCD 44 receives the light from the condenser lens 51 on a photo sensing surface 44a, converts the received light to electric charges and accumulates the charges. The accumulated charges are read out as image signals and sent to the AFE 45. Hereinafter, the image signal corresponding to the broadband light BE falling on the COD 44 will be referred to as a broadband image signal, whereas the image signals corresponding to the narrowband rays N1 to N4 falling on the CCD 44 will be referred to as first to fourth narrowband image signals respectively.

The AFE 45 is constituted of a correlated double sampling circuit (CDS), an automatic gain control circuit (AGC), and an analog-to-digital converter (A/D), which are not shown in the drawings. The CDS processes the image signal from the CCD 44 through correlated double sampling, to eliminate noises that may be caused by the drive of the COD 44. The AGC amplifies the image signal after the noise reduction through the CDS. The A/D converts the amplified image signal to a digital image signal of a predetermined bit number, and outputs the digital image signal to the processor 12.

Figure 3:
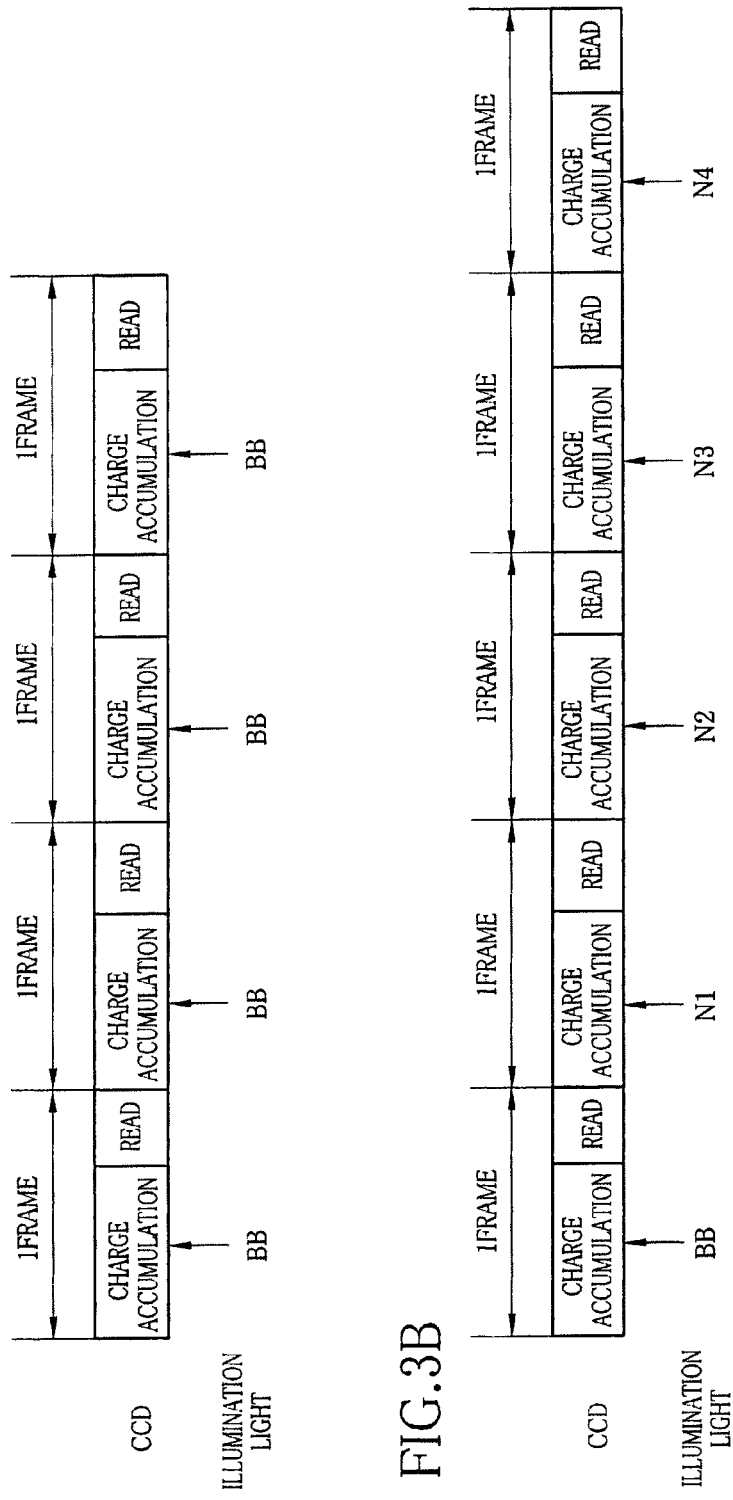
FIG. 3A is an explanatory diagram illustrating an imaging operation of a CCD in an ordinary inspection mode.
FIG. 3B is an explanatory diagram illustrating an imaging operation of the CCD in a search mode.

The imaging controller 46 is connected to the controller 62 in the processor 12, to send a drive signal to the CCD 44 in response to a corresponding instruction from the controller 62. Based on the drive signal from the imaging controller 46, the CCD 44 outputs the image signal to the AFE 45 at a designated frame rate. When the system 10 is set at the ordinary inspection mode, as shown in FIG. 3A, two operation steps are carried out during one frame capturing period: the broadband light BB being photo-electrically converted to electric charges and accumulated as the signal charges, and the accumulated signal charges being read as a broadband image signal. The system 10 repeats these operation steps so long as it is set at the ordinary inspection mode.

On the other hand, when the system 10 is switched from the ordinary inspection mode to the search mode, two operation steps are carried out during one frame capturing period: the broadband light BB being photo-electrically converted to electric charges and accumulated as the signal charges, and the accumulated signal charges being read as a broadband image signal, as shown in FIG. 3B. When the broadband image signal has completely been read out, electric charges obtaining through photo-electric conversion of the first narrowband ray N1 are accumulated as signal charges, and the accumulated signal charges are read out as a first narrowband image signal during a first frame capturing period. When the first narrowband image signal has completely been read out, electric charges obtained through photo-electric conversion of the second narrowband ray N2 are accumulated as signal charges, and the accumulated signal charges are read out as a second narrowband image signal in a second frame capturing period.

When the second narrowband image signal has completely been read out, electric charges obtained through photo-electric conversion of the third narrowband ray N3 are accumulated as signal charges, and the accumulated signal charges are read out as a third narrowband image signal in a third frame capturing period. Thereafter, electric charges obtained through photo-electric conversion of the fourth narrowband ray N4 are accumulated as signal charges, and the accumulated signal charges are read out as a fourth narrowband image signal in a fourth frame capturing period.

As shown in FIG. 2, the processor 12 includes a digital signal processor (DSP) 55, a frame memory 56, a display control circuit 58, a search unit 60, an ordinary image producer 200, and a special image producer 201, which are individually controlled by the controller 62. The DSP 55 processes the broadband image signal and the first to fourth narrowband image signals, as being output from the AFE 45 of the electronic endoscope, for color-separation, color-interpolation, white-balance adjustment, gamma correction and the like, to produce broadband image data and first to fourth narrowband image data. The frame memory 56 stores the broadband image data and the first to fourth narrowband image data from the DSP 55.

Figure 4:
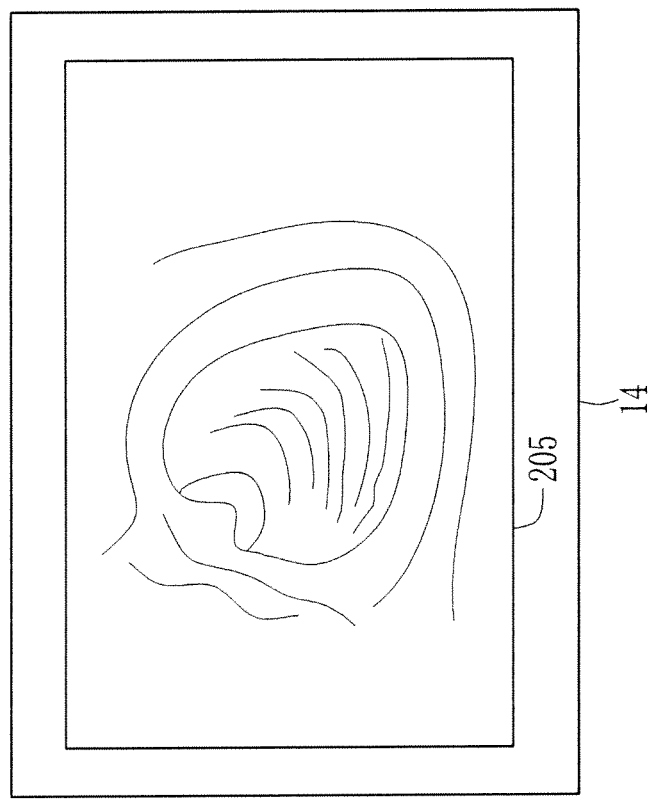
FIG. 4 is a view of an endoscopic image displayed on a monitor.

The ordinary light image producer 200 produces an ordinary light image 205 from the broadband image data stored in the frame memory 56. The special light image producer 201 produces a special light image 206 from one or more than one of the first to fourth narrowband image data stored in the frame memory 56. The display controller 58 controls the monitor 14 to display either an ordinary light image 205 or a special light image 206. In FIG. 4, an ordinary light image 205 is displayed on the monitor 14.

The search unit 60 includes a vascular information calculator 210, first and second associating sections 211 and 212, an image accumulator 213, a biological information input 214, and an image search section 215. The vascular information calculator 210 acquires information on blood vessels in the body cavity. The first associating section 211 associates the vascular information acquired by the vascular information calculator 210 with ordinary light images 205. The second associating section 212 associates the vascular information acquired by the vascular information calculator 210 with special light images 206. The image accumulator 213 stores the ordinary and special light images 205 and 206 after they are associated with the vascular information. The biological information input 214 is for inputting vascular information on a search target T. The image search section 215 searches for those images which are associated with the same vascular information as the search target T.

The vascular information calculator 66 calculates vascular information with respect to designated areas in the body cavity on the basis of the first to fourth narrowband image data. The vascular information may include blood vessel depth, blood concentration, and oxygen saturation. In the present embodiment, as shown in FIG. 5A, every ordinary light image or special light image is subdivided into nine segments A1 to A9, to acquire vascular information individually from these segments A1 to A9. Thus, a group of vascular information 220 is acquired from the respective segments A1 to A9 of every ordinary or special light image 205 or 206. How to acquire the vascular information will be described in detail later. Note that each image may be subdivided into less than or more than nine segments.

Among the vascular information, D stands for "vessel depth", wherein S stands for "superficial vessel", M "middle layer vessel", and D "deep layer vessel". Numbers following these symbols S, M and D indicate that the higher number represents the deeper zone within each layer. Also, C stands for "blood concentration", wherein L stands for "low blood concentration range", M "middle blood concentration range", and H "high blood concentration range". Numbers following these symbols L, M and H indicate that the higher number represents the higher blood concentration level within each range. Moreover, StO2 stands for "oxygen saturation", wherein L stands for "low oxygen range", M "middle oxygen range", and H "high oxygen range". Numbers following these symbols L, M and H indicate that the higher number represents the higher oxygen level within each range.

The first associating section 211 associates an individual ordinary image 205 with a group of vascular information 220 that is acquired from this ordinary image 205. The second associating section 212 associates an individual special image 206 with a group of vascular information 220 that is acquired from this special image 205. The image accumulator 213 stores these images 205 and 206 in association with their vascular information 220.

As shown in FIG. 6, the ordinary and special images 205 and 206 are stored time-sequentially in the image accumulator 213. For example, an ordinary light image 205a and a special light image 206a, which were captured at the same time t1, are stored in association with each other as well as with the vascular information 220 acquired at the same time t1.

Figure 7:
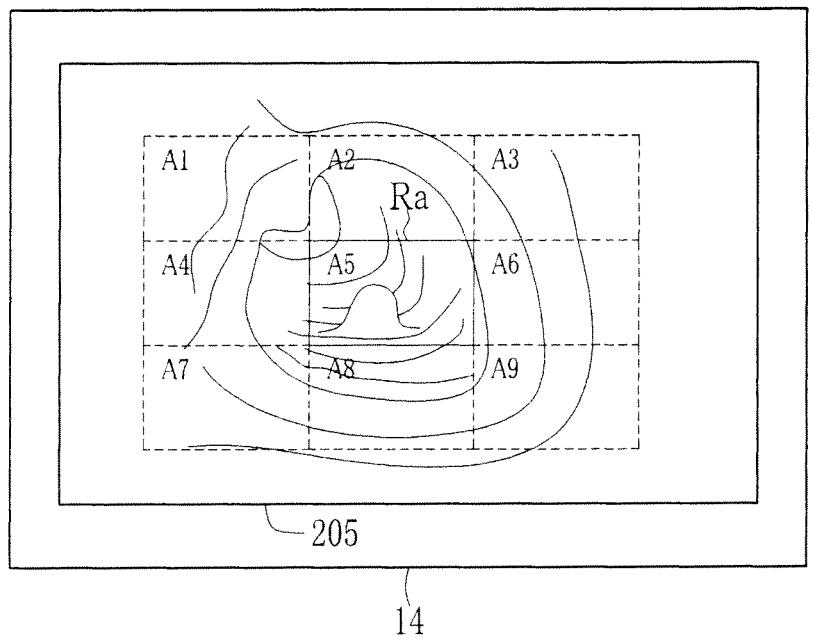
FIG. 7 is a view of an ordinary light image displayed on a monitor, with an area designating frame Ra superimposed thereon.

The vascular information input 214 includes an area framing section 214a, a lock-on section 214b and a vascular information detector 214c. The area framing section 214a is for displaying an area designating frame Ra in the ordinary or the special light image 205 or 206 on the monitor 14. The lock-on section 214b designates an area or body part inside the area designating frame Ra as a search target T when the operator presses a lock-on switch 25 of the endoscope 11 in the search mode, hereinafter referred to as the target lock-on operation. The vascular information detector 214c detects vascular information on the search target T from a group of vascular information associated with the image 205 or 206 displayed at the time of the lock-on operation. As shown for example in FIG. 7, the area framing section 214a displays the area designating frame Ra in any one of the segments A1 to A9 of the image 205 or 206 on the monitor 14.

The image search section 215 searches the image accumulator 213 for those ordinary or special light images 205 or 206 which are associated with the vascular information on the search target T. First, the latest ordinary and special light images 205 and 206 are extracted from the image accumulator 213. Then it is checked if any of the segments A1 to A9 of these latest images 205 and 206 has the same vascular information as for the search target T. If there is a segment that has the same vascular information as for the search target T, the area framing section 214a displays the area designating frame Ra in that area. If neither the latest ordinary light image 205 nor the latest special light image 206 contains any such segments that has the same vascular information as for the search target T, no area designating frame Ra is displayed on the monitor 14.

Thus the search target T can be found in the latest ordinary light image 205 or the latest special light image 206, which has been stored in association with a group of vascular information 220 acquired from the respective segments A1 to A9 of that image 205 or 206 in the image accumulator 213, by comparing the vascular information 220 of the individual segments A1 to A9 of each image 205 or 206 with the vascular information on the search target T, which has also been detected and memorized in response to the target lock-on operation.

As shown for instance in FIG. 8A, when a lesion is found on the inner wall of the body cavity, and the operator will check if there is a metastasis or another lesion around this lesion, the operator designates the lesion as a search target T through the target lock-on operation. Then vascular information on the search target T is detected in response to the target lock-on operation. Thereafter, the operator pushes and pulls the probing portion 16 inside the body cavity, scanning for another lesion. As a result, the initially-found lesion or the search target T may fade out of the monitor screen 14, as shown in FIG. 8B.

Once the search target T has faded out of the monitor screen 14, it can be difficult to find the search target T again by means of the pattern recognition as mentioned above in the description of the prior art. According to the present invention, since the vascular information on the search target T was acquired at the time of the target lock-on operation, and it is checked if any of the segments A1 to A9 of the latest images 205 and 206 has the same vascular information as the vascular information on the search target T, the area corresponding to the search target T can be found out again when the probing portion 16 comes back to a position where the just-captured image contains the same vascular information as for the search target T. Then the corresponding area to the search target T will be indicated by the area designating frame Ra on the monitor screen 14, as shown in FIG. 8C.

Figure 9:
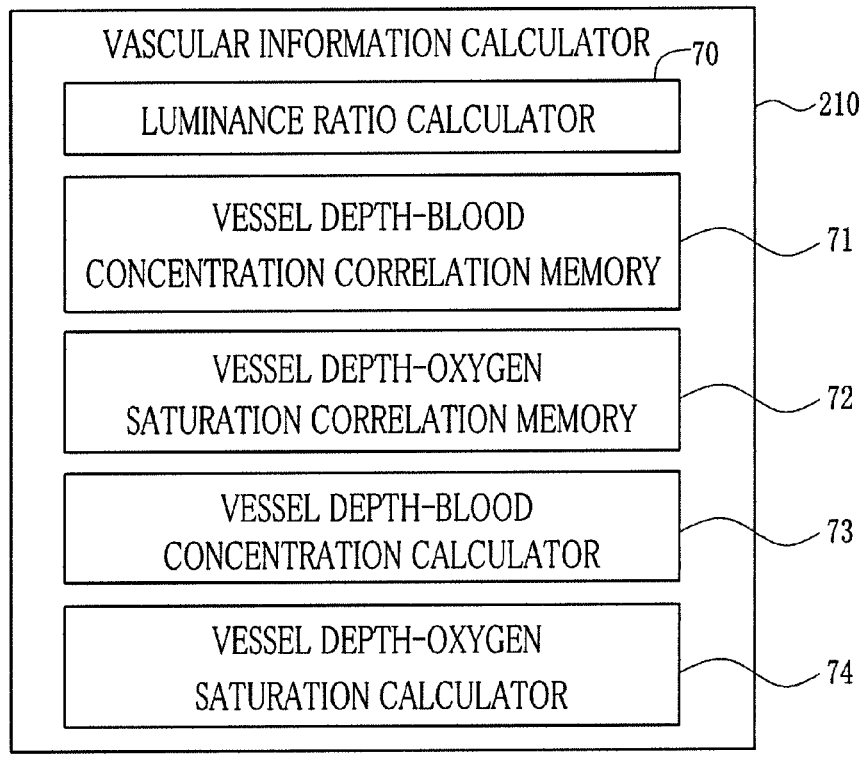
FIG. 9 is a block diagram illustrating a structure of a vascular information calculator.

As shown in FIG. 9, the vascular information calculator 210 includes a luminance ratio calculator 70, a vessel depth-blood concentration correlation memory 71, a vessel depth-oxygen saturation correlation memory 72, a vessel depth-blood concentration calculator 73, and a vessel depth-oxygen saturation calculator 74. The luminance ratio calculator 70 identifies such image areas that contain blood vessels, hereinafter called the vascular areas, on the basis of the first to fourth narrowband image data stored in the frame memory 56. For example, the vascular areas may be identified from the difference in luminance between blood vessels and other body parts.

The luminance ratio calculator 70 calculates a first luminance ratio S1 (=Log B1/B2) between the first and second narrowband images with respect to individual pixels in the vascular area, wherein B1 represents luminance of one pixel of the first narrowband image, and B2 represents luminance of a corresponding pixel of the second narrowband image, the corresponding pixels representing the same location of the subject. The luminance ratio calculator 70 also calculates a second luminance ratio S2 (=Log G/B2) between the second and third narrowband images, wherein G represents luminance of a corresponding pixel of the third narrowband image, which also represents the same location of the subject as the corresponding pixels of the first and second narrowband images. Moreover, the luminance ratio calculator 70 calculates a third luminance ratio S3 (=B4/B1) between the fourth and first narrowband images, and a fourth luminance ratio S4 (=B2/B1) between the second and first narrowband images, wherein B4 represents luminance of a corresponding pixel of the fourth narrowband image.

The vessel depth-blood concentration correlation memory 71 stores correlation between the first and second luminance ratios S1 and S2, blood concentration in the vessels (hemoglobin index), and blood vessel depth. This correlation may be previously acquired from analyses of an enormous amount of first to third narrowband image data obtained and accumulated through diagnoses and the like.

Figure 10:
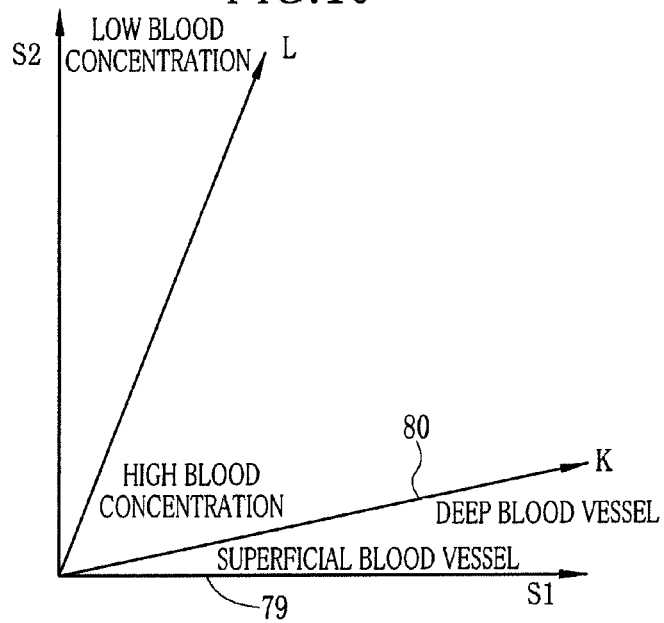
FIG. 10 is a graph showing correlations between first and second luminance ratios S1 and S2, and blood vessel depth and blood concentration.

The vessel depth-blood concentration correlation memory 71 stores the above correlation by correlating two coordinate systems 79 and 80, as shown in FIG. 10: luminance coordinate system 79 representing the first and second luminance ratios S1 and S2, and vascular information coordinate system 80 representing blood concentration and vessel depth. The vascular information coordinate system 80 is provided on the luminance coordinate system 79, and consists of a K-axis representing vessel depth and an L-axis representing blood concentration. The K-axis has a positive gradient to the luminance coordinate system 79 because the vessel depth has a positive correlation with the luminance coordinate system 79. The K-axis slopes upward from left to right and the vessel depth increases from left to right on the K-axis. The L-axis also has a positive gradient to the luminance coordinate system 79 because the vessel depth has a positive correlation with the luminance coordinate system 79. The L-axis slopes upward from left to right and the blood concentration decreases from left to right on the L-axis.

Figure 11:
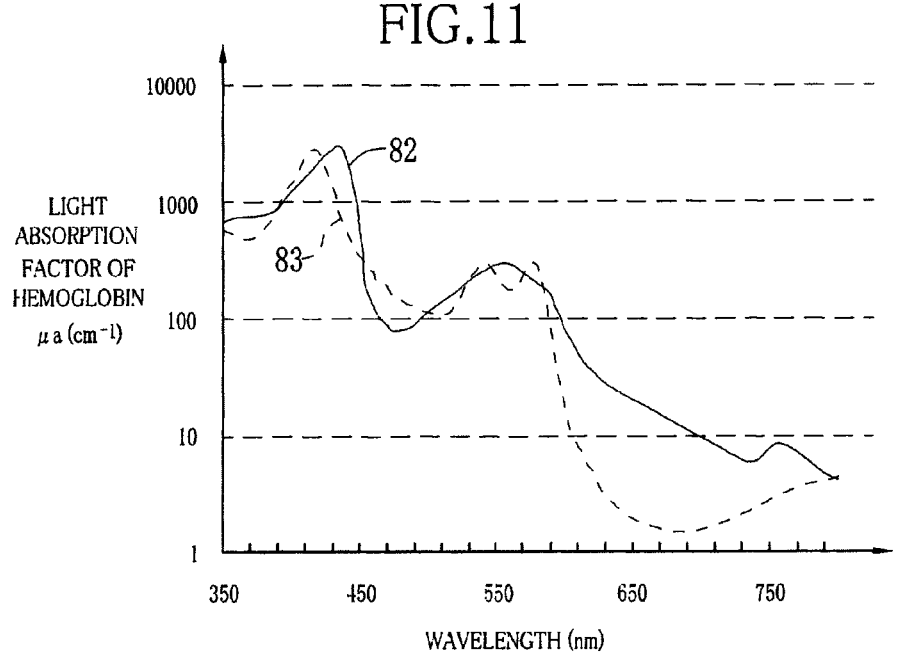
FIG. 11 is a graph showing light absorption coefficients of hemoglobin.

The vessel depth-oxygen saturation correlation memory 72 stores correlation between the third and fourth luminance ratios S3 and S4, the oxygen saturation in the vessels, and the blood vessel depth. This correlation may be previously acquired from analyses of an enormous amount of first, second and fourth narrowband image data obtained and accumulated through diagnoses and the like. As shown in FIG. 11, hemoglobin in the blood vessels has such light absorption characteristics that the light absorption coefficient $\mu a$ varies depending on the wavelength of the illumination light. The light absorption coefficient $\mu a$ indicates the degree of light absorbance of hemoglobin, i.e. the magnitude of light absorption in hemoglobin. The light absorption coefficient is a coefficient used in a formula expressing the attenuation of light projected onto hemoglobin: $Io \exp(-\mu a \times x)$, wherein Io stands for the intensity of light projected from a light source toward a subject tissue, and x(cm) stands for the depth to a blood vessel inside the subject tissue.

As shown in FIG. 11, reduced hemoglobin, which is not combined with oxygen, has a different light absorption characteristic curve 82 from a light absorption characteristic curve 83 of oxygenated hemoglobin that is combined with oxygen. Therefore, the light absorbance of the reduced hemoglobin differs from that of the oxygenated hemoglobin, except at isosbestic points (intersections between the curves 82 and 83), at which reduced hemoglobin and oxygenated hemoglobin have the same degree of light absorbance (the same light absorption coefficient $\mu a$). Because of the difference in light absorbance between reduced hemoglobin and oxygenated hemoglobin, the luminance of an identical blood vessel will vary depending upon the percentage of oxygenated hemoglobin in that vessel, even while the vessel is illuminated with light of constant intensity and wavelength. In addition, the light absorption coefficient $\mu a$ and hence the luminance will change with the wavelength of the illumination light, even while the light intensity is constant.

In view of the above light absorption characteristics of hemoglobin and the facts that the light absorbance of blood vessels will vary depending on the oxygen saturation, especially at wavelengths of 445 nm and 473 nm, and that rays of shorter wavelengths with shorter depths of reach are necessary in order to cover the wide depth range in extracting information about blood vessel depth, the first, second and fourth narrowband rays N1, N2 and N4 should preferably include at least a narrowband ray of a wavelength range having a center wavelength of not more than 450 nm. Moreover, even where the oxygen saturation is the same, if the wavelength of the illumination light is different, the light absorption coefficient will change, and hence the reaching depth of the illumination light into the mucous membrane will change. Accordingly, correlation between luminance ratio and blood vessel depth may be determined making use of the property of light that the depth of reach varies depending on the wavelength.

Figure 12:
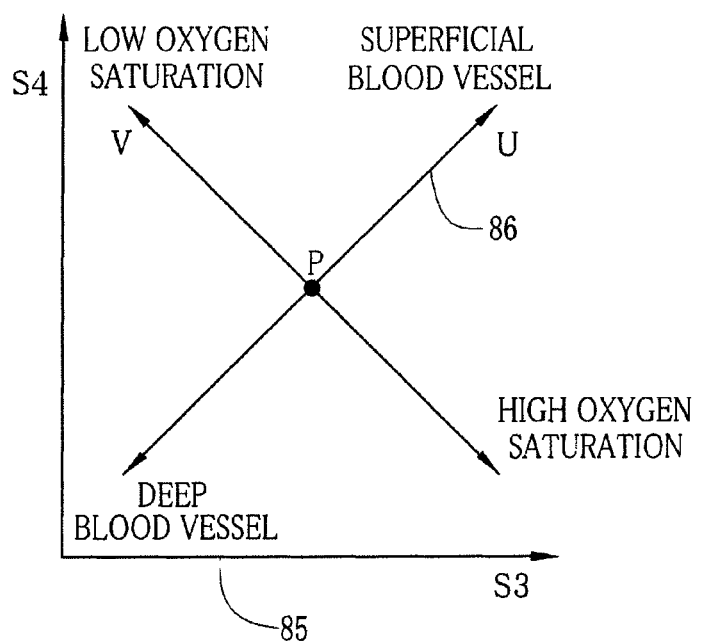
FIG. 12 is a graph showing correlation between third and fourth luminance ratios S3 and S4, and blood vessel depth and oxygen saturation.

The vessel depth-oxygen saturation correlation memory 72 memorizes the correlation between vessel depth and oxygen saturation, as shown in FIG. 12, wherein coordinates of a luminance coordinate system 85 representing the third and fourth luminance ratios S3 and S4 are correlated with coordinates of a vascular information coordinate system 86 representing oxygen saturation and blood vessel depth. The vascular information coordinate system 86 is a U-V coordinate system provided on the luminance coordinate system 85, wherein U-axis represents the blood vessel depth, and V-axis represents the oxygen saturation. The U-axis has a positive inclination because the blood vessel depth has a positive correlation to the luminance coordinate system 85. Concerning the U-axis, upper-right direction indicates decreasing blood vessel depth, and lower-left direction indicates increasing blood vessel depth. On the other hand, the V-axis has a negative inclination because the oxygen saturation has a negative correlation to the luminance coordinate system 85. Concerning the V-axis, upper-left direction indicates descending oxygen saturation, and lower-right direction indicates ascending oxygen saturation.

In the vascular information coordinate system 86, the U-axis and the V-axis orthogonally intersect at a point P. This is because the light absorbance to the fourth narrowband ray N4 has a reversed relation in magnitude to the light absorbance to the second narrowband ray N2. Specifically, as shown in FIG. 11, to the fourth narrowband ray N4 having the wavelength of 440±10 nm, the light absorption coefficient of reduced hemoglobin 82 is higher than the light absorption coefficient of oxygenated hemoglobin 83 having higher oxygen saturation than reduced hemoglobin. On the contrary, to the second narrowband ray N2 having the wavelength of 470±10 nm, the light absorption coefficient of oxygenated hemoglobin 83 is higher than the light absorption coefficient of reduced hemoglobin 82. The order in magnitude of the light absorption coefficient to the fourth narrowband ray N4 and the light absorption coefficient to the second narrowband ray N2 is reversed between the reduced hemoglobin 82 and the oxygenated hemoglobin 83. It is to be noted that the U-axis and V-axis would not be orthogonal if a ray of a wavelength range to which the magnitude relation in the light absorption coefficient is not reversed is used instead of the first, second and fourth narrowband rays N1, N2 and N4. Meanwhile, to the first narrowband ray N1 having the wavelength of 400±10 nm, the light absorption coefficient of oxygenated hemoglobin is approximately equal to that of reduced hemoglobin.

Figure 13A:
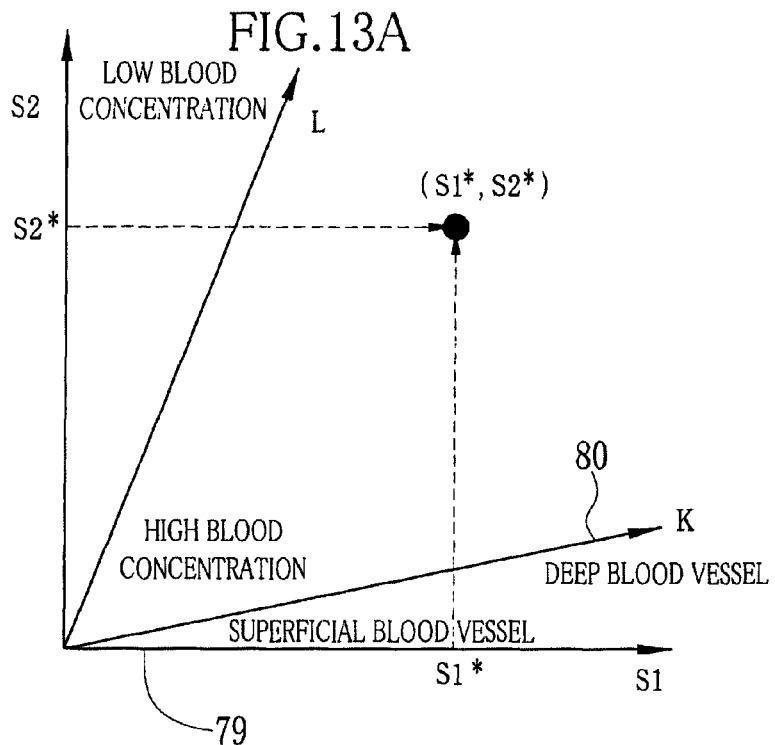
FIG. 13A is an explanatory diagram illustrating a method of determining coordinates (S1*, S2*) of the first and second luminance ratios in a luminance coordinate system.
Figure 13B:
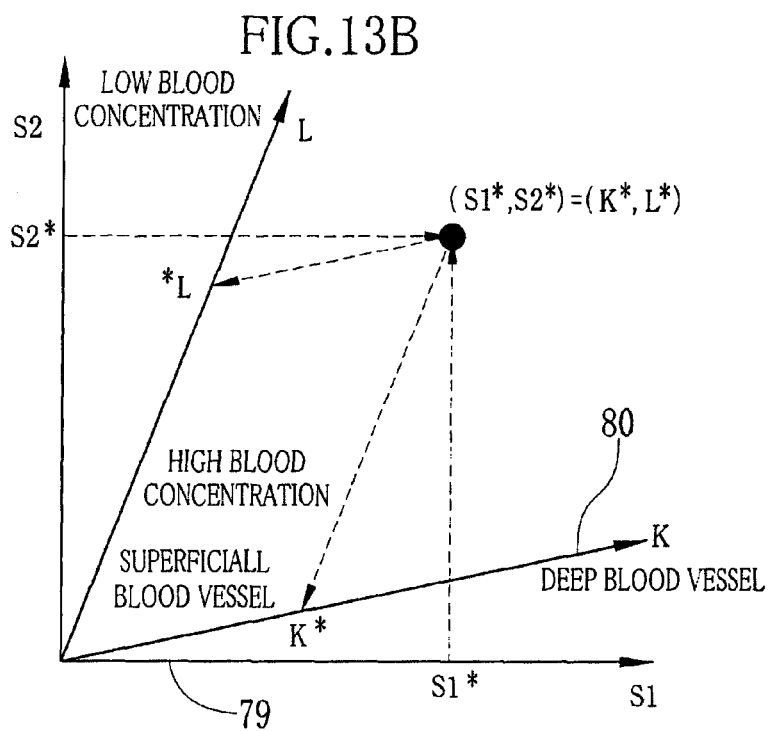
FIG. 13B is an explanatory diagram illustrating a method of determining those coordinates (K*, L*) in a vascular information coordinate system, corresponding to the coordinates (S1*, S2*)

The vessel depth-blood concentration calculator 73 determines coordinates (S1*, S2*) in the luminance coordinate system 79, as shown in FIG. 13A, these coordinates corresponding to the first and second luminance ratios S1* and S2* at a measured point. After determining the coordinates (S1*, S2*), the calculator 73 determines coordinates (K*, L*) in the vascular information coordinate system 80, corresponding to the coordinates (S1*, S2*), as shown in FIG. 13B. Thus, the blood vessel depth K* and the blood concentration L* are determined with respect to a particular pixel in the vascular area.

Figure 14A:
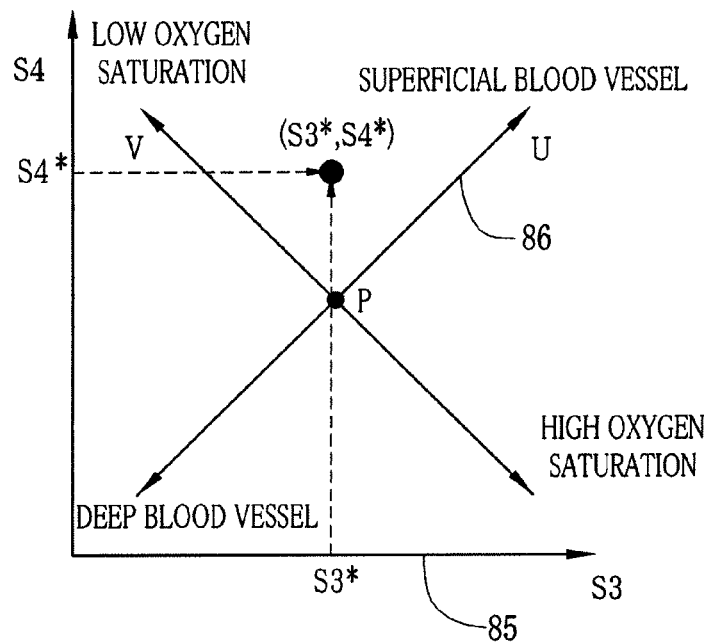
FIG. 14A is an explanatory diagram illustrating a method of determining coordinates (S3*, S4*) of the third and fourth luminance ratios in a luminance coordinate system.
Figure 14B:
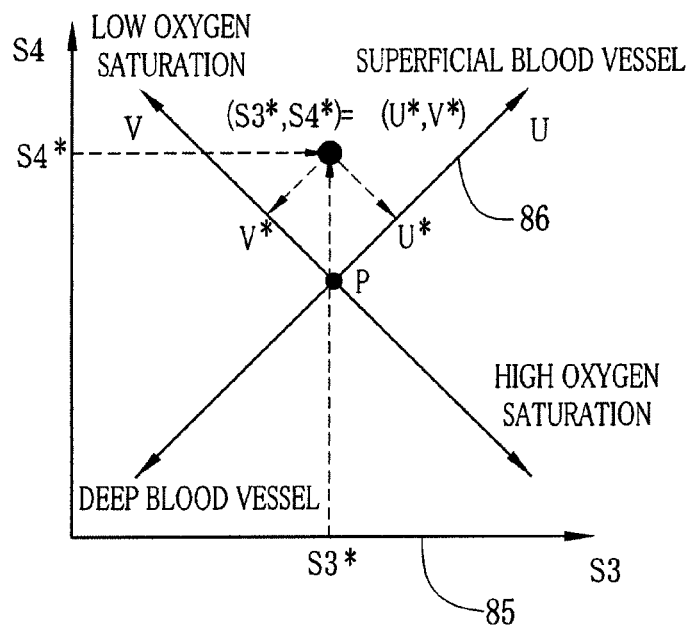
FIG. 14B is an explanatory diagram illustrating a method of determining coordinates (U*, V*) in a vascular information coordinate system, corresponding to the coordinates (S3*, S4*)

The vessel depth-oxygen saturation calculator 74 determines coordinates (S3*, S4*) in the luminance coordinate system 85, as shown in FIG. 14A, these coordinates corresponding to the third and fourth luminance ratios S3* and S4* at a measured point. After determining the coordinates (S3*, S4*), the calculator 74 determines coordinates (U*, V*) in the vascular information coordinate system 86, corresponding to the coordinates (S3*, S4*), as shown in FIG. 14B. Thus, the blood vessel depth U* and the oxygen saturation V* are determined with respect to a particular pixel in the vascular area.

Figure 15:
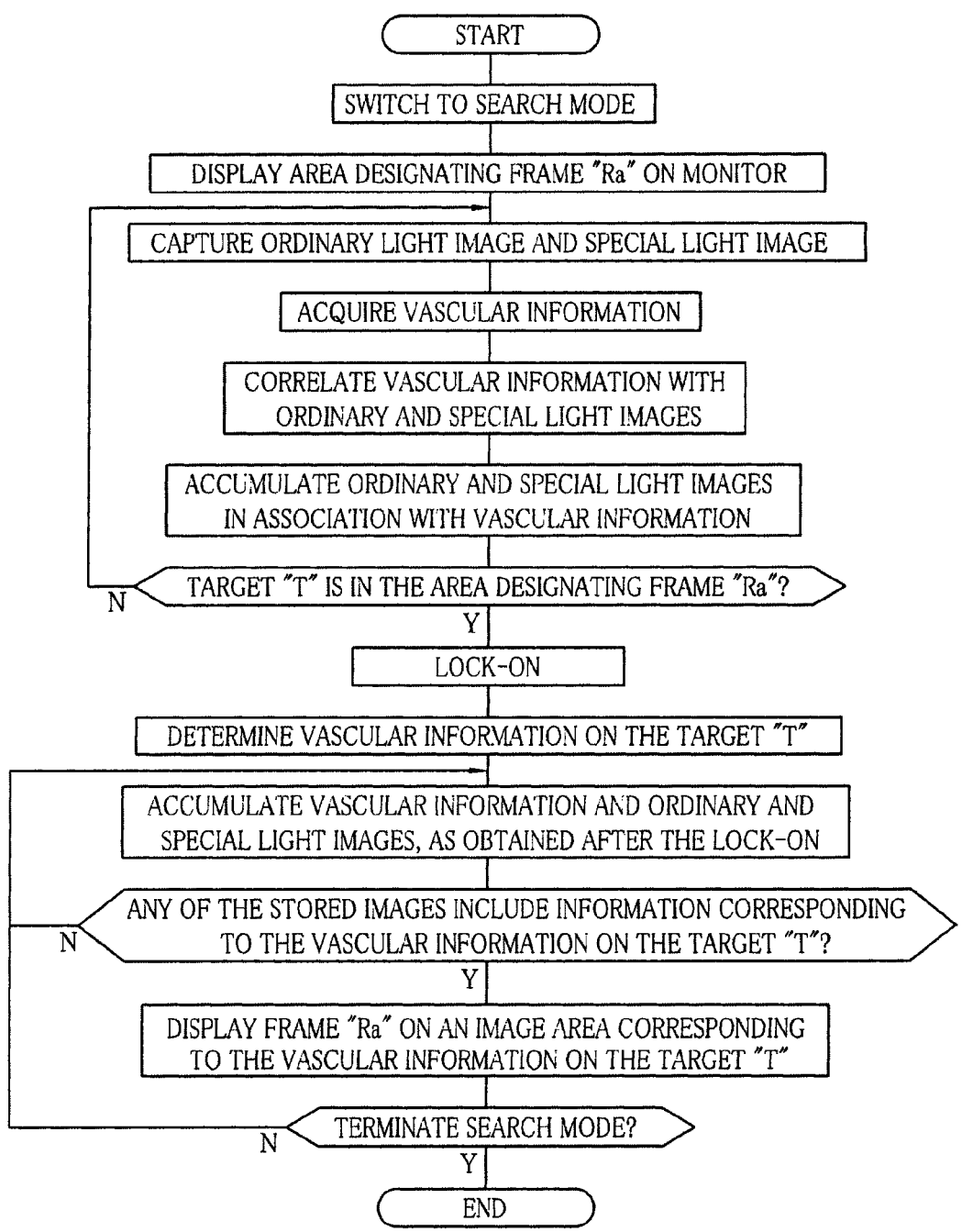
FIG. 15 is a flowchart illustrating the operation of the present invention.

Now the operation of the present invention will be described with reference to the flowchart shown in FIG. 15. First, the console 23 is operated to switch the electronic endoscope system 10 from the ordinary inspection mode to the search mode. When the system 10 is switched to the search mode, the area designating frame Ra is displayed on the monitor 14. Then ordinary light images 205 and special light images 206 are captured, and a group of vascular information 220 is acquired for each image from the first to fourth narrowband image data obtained under the illumination of the first to fourth narrowband rays N1 to N4. The vascular information 220 includes blood vessel depth, blood concentration and oxygen saturation in the respective body cavity areas sectioned by the segments A1 to A9 of every ordinary and special light image 205 and 206.

Thereafter the ordinary light image 205 and the special light image are associated with the corresponding vascular information 220, and are time-sequentially stored in the image accumulator 213. This operation sequence will be repeated for each image till a search target T is designated through the target lock-on operation.

In the target lock-on operation, the operator presses on the lock-on switch 25 when the search target T is confined in the area designating frame Ra. Then the vascular information on the search target T is extracted from the first to fourth narrowband data obtained at the moment when the lock-on switch 25 is pressed on. Thereafter, it is determined whether the latest image among the ordinary and special light images stored in the image accumulator 213 contains the same vascular information as for the search target T in any of its segments A1 to A9.

If it is determined that at least one of the segments A1 to A9 of the latest image 205 or 206 contains the same vascular information as for the search target T, the area designating frame Ra is displayed in the segment having the same vascular information as for the search target T on the latest image 205 or 206 that is presently displayed on the monitor 14. On the other hand, if the latest image 205 or 206 does not contain any segment that has the same vascular information as for the search target T, the area designating frame Ra is not displayed on the monitor 14, but only the latest image 205 or 206 is displayed. The procedure after the lock-on operation will be repeated so long as the system 10 is set in the search mode. When the system 10 is switched to from the search mode to the ordinary inspection mode, the search for the target T is terminated.

Figure 16:
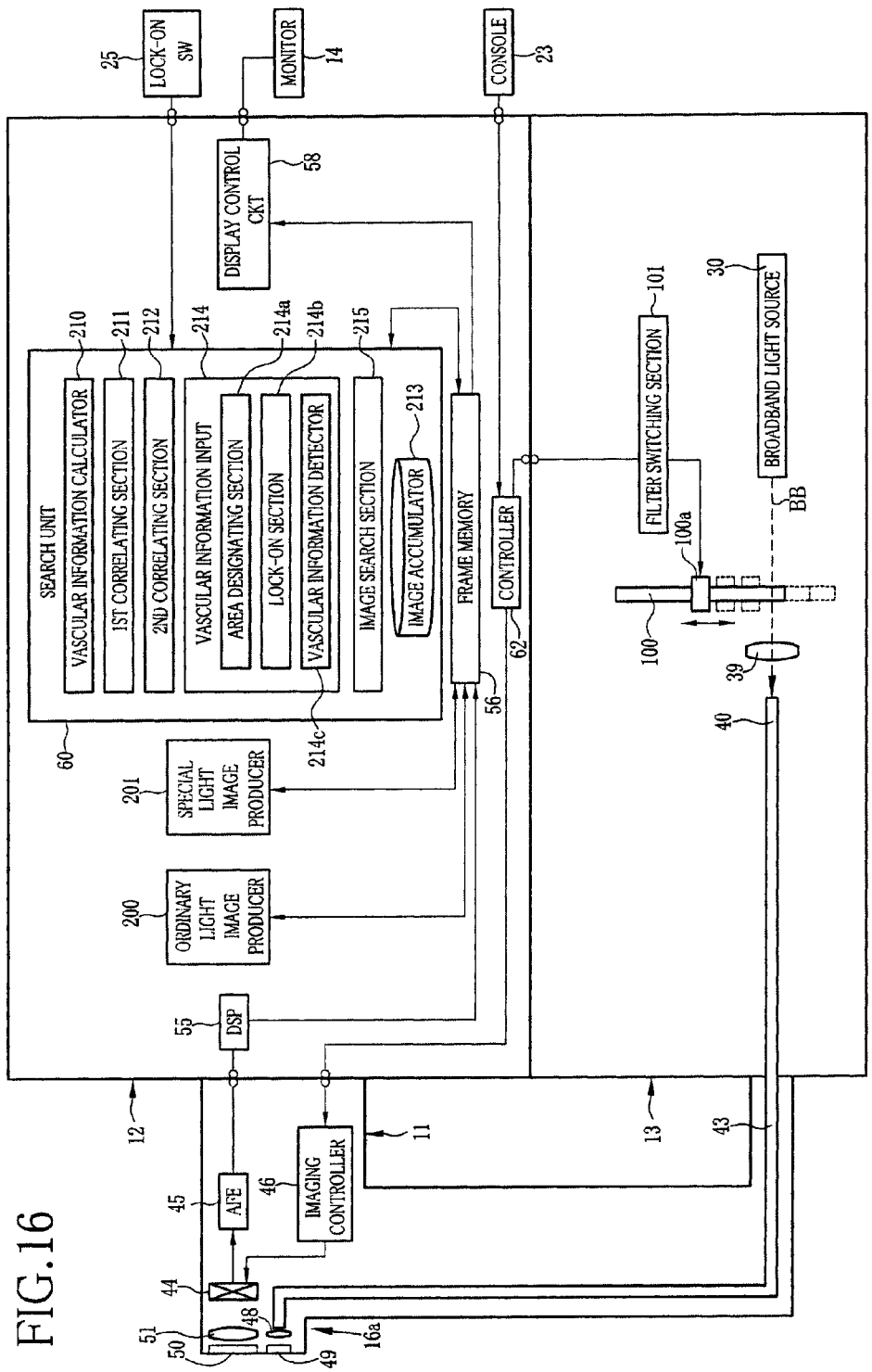
FIG. 16 is a block diagram illustrating the circuitry of an electronic endoscope system according to a second embodiment of the present invention.

In the above embodiment, the first to fourth narrowband light sources are used in addition to the broadband light source, for generating the first to fourth narrowband rays N1 to N4 in addition to the broadband light BB. In another embodiment, as shown in FIG. 16, the first to fourth narrowband light sources are not installed, but a rotary filter 100 is installed in between a broadband light source 30 and a condenser lens 39. The rotary filter 100 can rotate about a rotary axis 100a at a constant speed. The rotary filter 100 is also movable in its diagonal direction through a filter switching section 101 that is coupled to the rotary axis 100a.

Figure 17:
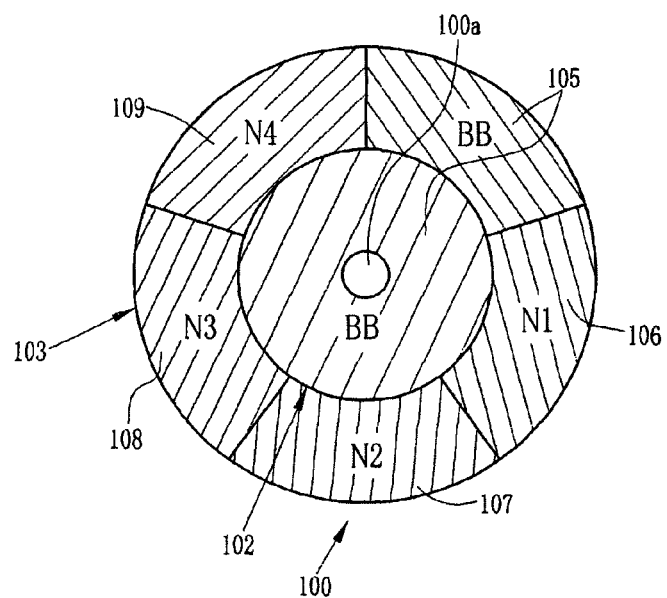
FIG. 17 is a schematic diagram illustrating a rotary filter used in the electronic endoscope system of FIG. 16.

As shown in FIG. 17, the rotary filter 100 includes two coaxial circular zones 102 and 103. The first zone 102 is for passing those light components of the broadband light BB which are used in the ordinary inspection mode. The second zone 103 is for passing those light components of the broadband light BB which are used in the ordinary light image capturing process and the special light image capturing process. Synchronously with the switching between these modes and processes, the filter switching section 101 moves the rotary filter 100 in a radial direction to set a suitable one of these zones 102 to 103 in the light path of the broadband light BB according to the expecting mode and process.

The first zone 102 includes a broadband light permeable sector 105 that allows the whole broadband light BB to pass through it. The second zone 103 includes first to fourth narrowband light permeable sectors 106, 107, 108 and 109, respectively allowing only one of the first to fourth narrowband rays N1 to N4 to pass through it among the light components of the broadband light BB. These sectors 106 to 109 are arranged in this order in the circumferential direction.

Figure 18:
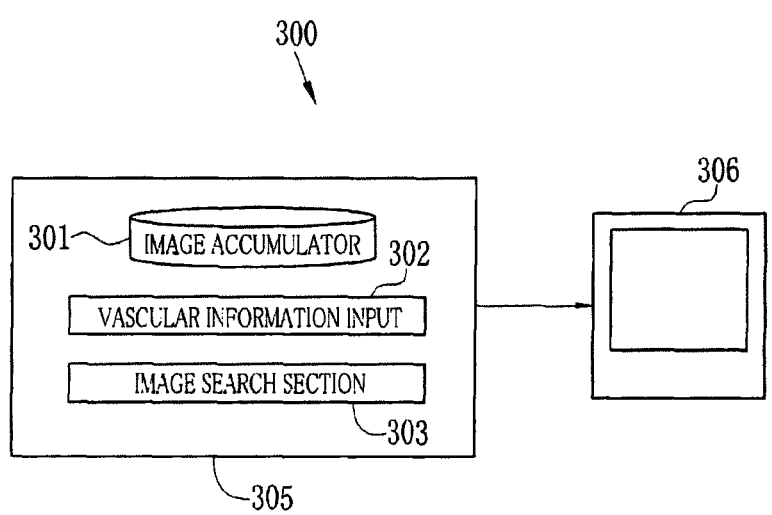
FIG. 18 is a block diagram illustrating an image search system of the present invention.

Referring to FIG. 18, an image search system 300 according to the present invention is illustrated. The image search system 300 is used for radiographic diagnoses based on a large number of endoscopic images that have been captured before. The image search system 300 consists of a main body 305 and a monitor 306. The main body 305 includes an image accumulator 301, a vascular information input 302, and an image search section 303.

The image accumulator 301 stores ordinary light images 205 and special light images 206, which have been captured from body cavities by endoscopes, each in association with a group of vascular information 220, acquired at the same time as each image-capturing. In the image accumulator 301, the ordinary and special light images 205 and 206 are time-sequentially stored in association with the vascular information, like in the first embodiment. The vascular information input 302 is an input device, such as a keyboard or a data interface, for inputting vascular information on a search target T.

The image search section 303 searches the image accumulator 301 for those ordinary or special light images 205 or 206 which are associated with the same vascular information as for the search target T. When an image 205 or 206 corresponding to the vascular information on the search target T is retrieved from among the images accumulated in the image accumulator 301, the retrieved image 205 or 206 is displayed on the monitor 306.

For example, as shown in FIG. 19A, when the input vascular information on the target T shows "D:M1, C:M1, StO2: H2", those vascular information 220 which have an area X corresponding to the vascular information "D:M1, C:M1, StO2:H2" are detected, and those images 205 or 206 which are associated with the vascular information 220 having the area X are extracted, as shown in FIG. 19B. Then the extracted ordinary light images 205 are displayed on the monitor 306 time-sequentially, randomly, or in another appropriate fashion, as shown in FIG. 19C. Thereafter the extracted special light images 206 are displayed on the monitor 306 in the same way as for the ordinary light images 205.

In the first embodiment where the target T is searched for while the endoscope is inserted in the body cavity, the vascular information on the target T is merely compared with the vascular information associated with the latest image among the images stored in the image accumulator 213. In the image search system of the present invention, on the other hand, the vascular information on the target T is compared with all the vascular information stored in association with the captured endoscopic images 205 and 206 in the image accumulator 301, in order to extract every image that includes the corresponding area X to the input vascular information on the search target T.

It is to be noted that the electronic endoscope system of the present invention may search multiple targets although the above embodiments have been described with respect to those cases where a single target is searched for. When multiple targets are designated, vascular information on these targets should be individually acquired and stored in a memory. In the above embodiment, vessel depth, blood concentration, and oxygen saturation are used as the vascular information for the image-searching. However, the search process may be executed based on at least one of these factors.

Although a target search is executed using vascular information on the target in the above embodiment, the search may be executed based on other biological information on the target than the vascular information, e.g. pit patterns, vessel structures, and/or vessel diameters. Instead of blood vessels, such body parts that contain autofluorescent components, such as collagen, NADH, and FAD, may serve as the search target among subject tissues inside the body cavity. In that case, the search target containing an autofluorescent component is illuminated with an exciting light, e.g. a narrowband ray of 405 nm, to generate intrinsic fluorescence. Light intensity or other information on the generated intrinsic fluorescence is used for the tracing process. Moreover, it is possible to inject an oncotropic photo-sensitive substance or fluorescent agent, such as porphyrin derivatives, into a patient and project an exciting light, e.g. a narrowband ray of 405 nm, onto a body site that might be affected by a tumor. Since the fluorescent agent accumulated in the tumor generates fluorescence then, the light intensity or other information on the generated fluorescence may be used for tracing the tumor as a target.

According to this embodiment, an electronic endoscope system comprises:
a special light projecting device for projecting special light into a body cavity, the special light having a different wavelength range from white light;
an imaging device for obtaining image signals through imaging the body cavity at constant intervals while projecting the special light into the body cavity;
an image producing device for producing special light images sequentially based on the image signals;
a biological information acquiring device for acquiring biological information from the image signals;
an associating device for associating the biological information acquired by the biological information acquiring device with an image corresponding to the image signal from which this biological information has been acquired;
an input device for inputting biological information on a search target; and
a search device for searching for an image that is associated with the same biological information as the input biological information on the search target among the special light images which have been associated with the biological information, wherein the special light projecting device can project an exciting light for causing subject tissues inside the body cavity to generate fluorescent light, and the biological information acquiring device acquires information on the fluorescent light as the biological information through imaging the generated fluorescent light.

The biological information acquiring device may preferably acquire pit patterns as the biological information in addition to or instead of the information on the fluorescent light.

In the illustrated embodiment, the area designating frame is automatically displayed on the monitor with the start of the search mode so that the operator may designate a body part inside the frame as a search target. In another alternative embodiment, the area designating frame may be displayed when the operator designates a target using a pointer of the mouse or the like, so that the designated target will be surrounded by the frame.

The present invention is not only applicable to an electronic endoscope having a probing portion introduced into the body cavity, but also to a capsule type electronic endoscope having an imaging device like a CCD and other components integrated into a capsule.

It should be understood that the present invention is not to be limited to the above embodiments, but many variations and modifications of the present invention will be possible for those skilled in the art without departing from the scope of the present invention as specified in the appended claims.

What is claimed is:
1. An electronic endoscope system comprising:
an imaging device for obtaining image signals through imaging an interior of a body cavity at constant intervals;
an image producing device for producing images sequentially based on the image signals;
a special light projecting device for projecting special light into the body cavity, said special light having a different wavelength range from white light;
a biological information acquiring device for acquiring biological information from image signals obtained while said special light is being projected into the body cavity;
an associating device for associating the biological information acquired by said biological information acquiring device with an image corresponding to the image signal from which this biological information has been acquired;
an input device for inputting biological information on a search target;
a search device for searching for an image that is associated with the same biological information as the input biological information on the search target among the images which have been associated with the biological information by said associating device;
a display device for displaying images produced by said image producing device;
an area designating frame display device for displaying an area designating frame on an image displayed on said display device; and
a lock-on device for designating a portion confined in said area designating frame as a search target, wherein said input device inputs the biological information on the designated search target on a basis of biological information acquired from the image signal obtained at the time when the search target is designated.

2. The electronic endoscope system as recited in claim 1, wherein when an image associated with the same biological information as the input biological information on the search target is displayed on said display device, said area designating frame display device displays the area designating frame on a portion of the displayed image, the portion corresponding to the biological information on the search target.

3. The electronic endoscope system as recited in claim 1, further comprising a white light projecting device for projecting white light into the body cavity, wherein
said image producing device produces special light images from image signals obtained through imaging the interior of the body cavity illuminated with said special light, and ordinary light images from image signals obtained through imaging the interior of the body cavity illuminated with said white light;
said associating device associates the biological information acquired by said biological information acquiring device with a special light image or an ordinary light image that corresponds to the image signal from which this biological information has been acquired; and
said search device searches for those special or ordinary light images which are associated with the same biological information as the biological information on the designated search target.

4. The electronic endoscope system as recited in claim 1, wherein the biological information acquired by said biological information acquiring device includes vascular information including at least one of blood vessel depth, blood concentration, and oxygen saturation.

5. The electronic endoscope system as recited in claim 4, wherein said special light projecting device is adapted to project at least three narrowband rays onto subject tissues including blood vessels in the body cavity, said at least three narrowband rays having different wavelength ranges from each other within a range of 400 nm to 600 nm, including a blue ray band and a green ray band, and wherein
said biological information acquiring device comprises
a first narrowband signal obtaining device for obtaining a plurality of narrowband signals corresponding respectively to the narrowband rays from among the image signals obtained by said imaging device, and
a first vascular information acquiring device for acquiring vascular information including information on blood vessel depth and blood concentration on the basis of said plurality of narrowband signals.

6. The electronic endoscope system as recited in claim 5, wherein said first narrowband signal obtaining device obtains first and second narrowband signals corresponding to first and second narrowband rays having different wavelength ranges from each other in the blue ray band, and a third narrowband signal corresponding to a third narrowband ray in the green ray band.

7. The electronic endoscope system as recited in claim 6, wherein the first narrowband ray has a wavelength range of 405±10 nm, the second narrowband ray has a wavelength range of 470±10 nm, and the third narrowband ray has a wavelength range of 560±10 nm.

8. The electronic endoscope system as recited in claim 4, wherein said special light projecting device is adapted to project a plurality of narrowband rays onto subject tissues including blood vessels in the body cavity, said plurality of narrowband rays having different wavelength ranges from each other, at least one of the different wavelength ranges having a center wavelength of 450 nm or less, and wherein
said biological information acquiring device comprises
a second narrowband signal obtaining device for obtaining a plurality of narrowband signals corresponding respectively to the narrowband rays from among the image signals, and
a second vascular information acquiring device for acquiring vascular information including information on blood vessel depth and oxygen saturation on the basis of said plurality of narrowband signals.

9. The electronic endoscope system as recited in claim 8, wherein each of said plurality of narrowband rays includes a wavelength, to which oxygenated hemoglobin shows a different degree of light absorbance from reduced hemoglobin, and said plurality of narrowband signals vary differently from each other depending on oxygen saturation of blood.

10. An image search system comprising:
an image accumulator for storing special light images obtained through imaging an interior of a body cavity illuminated with special light that has a different wavelength range from white light, in association with biological information on the body cavity acquired at the same time as the special light images;
an input device for inputting biological information on a search target; and
a search device for searching for those special light images which are associated with the same biological information as the input biological information on the search target among the special light images stored in said image accumulator;
a display device for displaying images stored in said image accumulator;
an area designating frame display device for displaying an area designating frame on an image displayed on said display device; and
a lock-on device for designating a portion confined in said area designating frame as a search target, wherein
said input device inputs the biological information on the designated search target on a basis of biological information acquired from an image signal obtained at a time when the search target is designated.

11. A processor for an electronic endoscope, comprising:
a receiving device for receiving image signals that are obtained at constant intervals by said electronic endoscope through imaging an interior of a body cavity illuminated with special light having a different wavelength range from white light;
an image producing device for producing special light images sequentially from the image signals;
a biological information acquiring device for acquiring biological information on the interior of the body cavity from the image signals;
an input device for inputting biological information on a search target;
a search device for searching for those special light images which are associated with the same biological information as the input biological information on the search target;
a display device for displaying images produced by said image producing device;
an area designating frame display device for displaying an area designating frame on an image displayed on said display device; and
a lock-on device for designating a portion confined in said area designating frame as a search target, wherein said input device inputs the biological information on the designated search target on the basis of biological information acquired from the image signal obtained at the time when the search target is designated.

12. An image search method comprising:
producing special light images sequentially based on image signals obtained through imaging an interior of a body cavity at constant intervals while projecting special light into the interior of the body cavity, said special light having a different wavelength range from white light;
acquiring biological information on the interior of the body cavity from the image signals;
associating the acquired biological information with the special light images;
inputting biological information on a search target; and
searching for those special light images which are associated with the same biological information as the input biological information on the search target;
displaying images produced by said producing;
displaying an area designating frame on an image being displayed; and
designating a portion confined in said area designating frame as a search target, wherein said inputting inputs the biological information on the designated search target on a basis of biological information acquired from the image signal obtained at a time when the search target is designated.

13. The image search method as recited in claim 12, further comprising:
producing ordinary light images sequentially based on image signals obtained through imaging the interior of the body cavity at constant intervals while projecting white light into the interior of the body cavity;
associating each of the ordinary light images with a corresponding special light image and acquired biological information;
extracting those ordinary light images which are associated with the same biological information as the input biological information on the search target; and
displaying the extracted ordinary light images such that an area having the same biological information as the input biological information on the search target is distinguishable from other areas in each of the displayed ordinary light images.

* * * * *